United States Patent [19]

Lowry

[11] Patent Number: Plant 7,730

[45] Date of Patent: Dec. 3, 1991

[54] "ROYAL FORELLE" PEAR TREE

[75] Inventor: David B. Lowry, Talent, Oreg.

[73] Assignee: Associated Fruit Company, Phoenix, Oreg.

[21] Appl. No.: 500,241

[22] Filed: Mar. 26, 1990

[51] Int. Cl.[5] ..... A01H 5/00

[52] U.S. Cl. ..... Plt./36

[58] Field of Search ..... Plt./36

[56] References Cited

U.S. PATENT DOCUMENTS

P.P. 4,315 10/1978 Lowry ..... Plt. 36

OTHER PUBLICATIONS

Brooks, R. M., et al., "Royal Red" (listing from Pear *Register of New Fruit and Nut Varieties* 2nd Ed. 1972) Univ. of Calif., Press Berkeley, p. 462.

*Primary Examiner*—James R. Feyrer

*Attorney, Agent, or Firm*—Worrel & Worrel

[57] ABSTRACT

A new and distinct variety of pear tree which is somewhat remotely similar to the Bartlett, Forelle, and Comice pear trees (all unpatented), but from which it is distinguished as a large, vigorous, upright and hardy pear tree which is a regular and very productive bearer of large symmetrical fruit of good dessert quality having a thick, smooth, waxen, glossy skin; the skin having an occasional yellow ground color nearly all overspread, in maturity of ripening, with a burgundy red coloration, and the flesh being distinctly white.

1 Drawing Sheet

BACKGROUND OF THE NEW VARIETY

The present invention relates to a new and distinct variety of pear tree which will hereinafter be denominated varietally as "Royal Forelle" and more particularly to a pear tree which produces fruit which are mature for the first commercial harvesting approximately August 30 in Jackson County, near Phoenix, Oreg., ripening in storage within thirty days, and which can be harvested until approximately October 15 and further is distinguished principally as to novelty by producing a large, burgundy red, flavorful fruit, the flesh of which is distinctly white, and which has noteworthy storage and shipping characteristics.

Development of commercially successful varieties of fruit trees is a science which requires not only careful attention to the developmental sciences, but also enormous expenditures of time and effort in observing a multitude of potential varieties, recording their characteristics both favorable and unfavorable, comparing these characteristics of the varieties among themselves and to prior art varieties, and hopefully selecting a new variety suitable for commercialization which has attributes not theretofore available.

The present variety of pear tree constitutes one such new variety which is demonstrably superior in several characteristics to those commercial varieties of pear trees which have gone before. Even marginal improvements over existing varieties can result in a variety of immense commercial success. The achievement of favorable distinctions in several characteristics is truly noteworthy. Thus, the present variety is a tree of somewhat more upright bearing than the Bartlett pear tree (unpatented) and more closely related in this respect to the Forelle pear tree (unpatented). The fruit of the new variety is distinct from that of other commercial varieties in its burgundy red blush which, in maturity, is uniform about the fruit and does not have a striped appearance which is characteristic of known commercial varieties. The flesh of the new variety is distinctly white in comparison with the slightly yellowish-white flesh of the Bartlett pear tree and has superior keeping qualities. Importantly, the new variety is more resistant to pear blight than the Forelle pear tree and does not demonstrate a susceptibility to any form of virus nor any unusual susceptibility to insects or diseases.

Since the "Royal Forelle" is the result of a cross between the "Red Bartlett" and "Forelle" pear trees, it is a sibling of the "Red Angelo" pear tree (U.S. Plant Pat. No. 4,315) and thus shares many similarities with the "Red Angelo" pear tree. However, there are numerous distinctive differences between the "Royal Forelle" pear tree of the present invention and the "Red Angelo" pear tree. The "Royal Forelle" pear tree of the present invention is considerably more vigorous in growth producing many more and longer new growth shoots than the "Red Angelo" pear tree. In contrast, the "Red Angelo" pear tree has a distinctive tendency to produce short new growth and spurs, the spurs producing the fruit. As a consequence, the "Royal Forelle" pear tree of the present invention is less compact than the "Red Angelo" pear tree. The leaves of the "Royal Forelle" pear tree are more sharply pointed and less coarsely serrated than those of the "Red Angelo" pear tree. The new growth is reddish, maturing into dark green with a bronze reddish sheen. The stems of the leaves are pink.The leaves of the "Royal Forelle" pear tree are vigorous and tightly bunched to a greater degree than those of the "Red Angelo" pear tree.

The most significant differences between the "Royal Forelle" pear tree of the present invention and the "Red Angelo" pear tree are in regard to the fruit of the respective varieties. The fruit of the "Royal Forelle" pear tree is consistently larger than the fruit of the "Red Angelo" pear tree. The fruit of the "Royal Forelle" is symmetrical although a small percentage are roundish, having very little noticeable neck. The fruit of the "Royal Forelle" pear tree is thus less uniform than that of the "Red Angelo" pear tree. The fruit of the variety of the instant invention is considerably more smooth and heavily waxed in contradistinction to that of the "Red Angelo" pear tree. As to color, the fruit of the "Royal Forelle" pear tree is virtually totally red with a slight yellow under color as distinct from that of the "Red Angelo" pear tree. The fruit of both trees is characterized by the spotting and freckling of their common parent, the "Forelle" pear tree. The flavor of both is similar with the most noticeable difference being that the fruit of the new variety is not quite so sweet.

ORIGIN AND ASEXUAL REPRODUCTION OF THE NEW VARIETY

The present variety of pear tree hereof was originated by the inventor on his ranch which is located in Jackson County, near Phoenix, Oreg. The present variety is a cross between the Red Bartlett and Forelle pear trees (both unpatented). When the hybrid seedlings resulting from such cross pollination grew to maturity and bore fruit, one such seedling, that of the present variety, evidenced novel and distinct characteristics. Upon recognition of such characteristics by the inventor in 1978, it was selected for asexual reproduction. The present variety of pear tree was asexually reproduced by grafts on young pear trees in 1984 in an orchard on the aforesaid ranch. In maturity, the asexually reproduced trees of the new variety were identical to the parent tree in all respects.

SUMMARY OF THE NEW VARIETY

The "Royal Forelle" pear tree is characterized as to novelty as a large, vigorous, upright tree which is rapid growing and hardy and is a very productive bearer of uniform, generally symmetrical fruit of good dessert quality, having a skin with some yellow ground color substantially overspread, at maturity of ripening, with a burgundy red coloration and having flesh which is distinctly white. The fruit of the new variety is ripe for its first commercial harvesting approximately August 30 in Jackson County, near Phoenix, Oreg., fully ripening for consumption within thirty (30) days in storage, and being available for its last picking approximately October 15 in the same locale.

BRIEF DESCRIPTION OF THE DRAWING

The accompanying drawing is a color photograph of mature fruit of the new variety showing the base of one, a second in side elevation, a third in side elevation, a fourth sectioned in a longitudinal plane and laid open to show the distinctive white flesh and a fifth in plan view; a representative branch; and representative foliage.

DETAILED DESCRIPTION

Referring more specifically to the pomological details of this new and distinct variety of pear tree, the following has been observed under the ecological conditions prevailing at the ranch or origin which is located in Jackson Country, near Phoenix, Oreg. All major color code designations are by reference to the *Dictionary of Color,* by Maerz and Paul, Second Edition, 1950. Common color names are also employed occasionally.

TREE

Generally:

*Size.*—Large.

*Vigor.*—Vigorous. Considerably more vigorous than the "Red Angelo" pear tree and having the tendency to produce many more and longer new growth shoots than the "Red Angelo" pear tree.

*Figure.*—Vase-formed.

*Productivity.*—Very productive.

*Regularity of bearing.*—Regular bearer.

*Growth.*—Upright, tall, rapid. Less compact than the "Red Angelo" pear tree.

Trunk:

*Size.*—Medium.

*Surface texture.*—Medium.

Branches:

*Size.*—Medium.

*Surface texture.*—Smooth.

*Color.*—Mature Branches — Brownish gray. Immature Branches — Red.

*Lenticels.*—Numbers — Medium. Size — Medium.

CLEAVES

Size:

*Generally.*—Large.

*Length.*—Long — 6.35 cm to 8.89 cm (2½" to 3½").

*Width.*—Wide — 3.81 cm to 5.715 cm (1½" to 2¼").

Form: Sharply pointed; ovate. More sharply pointed than the leaves of the "Red Angelo" pear tree.

Thickness: Medium.

Color:

*Upwardly disposed surface.*—Red (4-K-11) shading to darker red (7-L-7).

*Downwardly disposed surface.*—Samovar yellow (12-K-7).

Texture: Smooth.

Leaf margin: Crenate; medium serrate. Less coarsely serrated than leaves of the "Red Angelo" pear tree.

Petiole:

*Length.*—2.54 cm to 3.81 cm (1" to 1½").

*Thickness.*—Medium.

New growth:

*Color.*—Reddish, maturing into dark green with a bronze reddish sheen. The stems of the leaves are pink.

Growth characteristics: Vigorous and tightly bunched to a greater degree than the leaves of the "Red Angelo" pear tree.

FLOWERS

Flower buds:

*Size.*—Medium.

*Surface texture.*—Somewhat shaggy on initial opening.

Date of bloom: April 20; slightly later than Bartlett pear tree.

Size:

*Generally.*—Medium.

Petals:

*Color.*—Pink on opening, turning to white at full bloom.

Fertility: Fertile.

Pollination: Can be pollinated by several varieties of pear trees including the "Red Angelo" pear tree and the "Bartlett" pear tree.

FRUIT

Maturity when described: Ripe for first commercial harvesting approximately August 30, ripening within thirty day storage period thereafter, and available for last picking approximately October 15 in Jackson County, near Phoenix Oreg. The fruit hangs well during season.

Size:

*Generally.*—Very large to medium, uniform. Consistently larger than the fruit of the "Red Angelo" pear tree.

*Average length.*—7.62 cm (3").

Form:

*Uniformity.*—Obovate.

*Symmetry.*—Symmetrical and somewhat variable. Less uniform than fruit of the "Red Angelo" pear tree.

Stem cavity:

*Generally.*—Acute; smooth.

*Width.*—Narrow.

*Depth.*—Medium.

*Shape.*—Symmetrical.

Stem:

*Generally.*—Medium length — Average 1.905 cm ($\frac{3}{4}''$).

*Thickness.*—Medium.

Calyx: Closed; Medium small.

Lobes: No separation at base; short; broad; obtuse.

Basin: Medium depth; medium width; symmetrical; rounded; obtuse; fairly smooth.

Skin:

*Thickness.*—Thick.

*Texture.*—Smooth; waxen; glossy. Considerably more smooth than the skin of the "Red Angelo" pear tree.

*Color.*—Yellow (11-L-5) ground color nearly all overspread in maturity with burgundy red (7-J-6) coloration with numerous medium size submerged red dots.

Flesh:

*Color.*—White (9-B-1).

*Juice production.*—Juicy.

*Flavor.*—Subacid.

*Aroma.*—Aromatic.

*Texture.*—Firm; fine; tender.

*Eating quality.*—Good. Not quite as sweet as the flesh of the "Red Angelo" pear tree.

*Core.*—Medium size; closed; axile.

*Core lines.*—Meeting.

*Calyx tube.*—Length — Medium.

*Calyx width.*—Medium.

*Calyx form.*—Funnel shaped.

Seed: Medium; plump; acute.

Use: Dessert market.

Keeping quality: Good — up to 20 weeks.

Resistance to disease: Midway between Bartlett and Forelle pear trees; being more resistant to pear blight than Forelle pear tree. Does not demonstrate any form of virus, and no unusual problems with insects or diseases. Extreme resistance to decay from storage rot.

Shipping and handling quanities: Good.

Although the new variety of pear tree possesses the described characteristics noted above as a result of the growing conditions prevailing in Jackson County, near Phoenix, Oreg., it is to be understood that variations of the usual magnitude and characteristics incident to changes in growing conditions, fertilization, pruning and pest control are to be expected.

Having thus described and illustrated my new variety of pear tree, what I claim as new and desire to be secured by Plant Letters Patent is:

1. A new and distinct variety of pear tree substantially as illustrated and described and which is somewhat remotely similar to the "Red Angelo" pear tree, (U.S. Plant Pat. No. 4,315) but from which it is distinguished by having considerably more vigorous growth including longer shoots and leaves more tightly bunched and producing fruit which are consistently larger but less uniform with skin which is more smooth and heavily waxed, and which is characterized at maturity by a skin coloration of burgundy red with a yellow under coloration with medium size submerged red dots and which has distinctively white flesh.

* * * * *

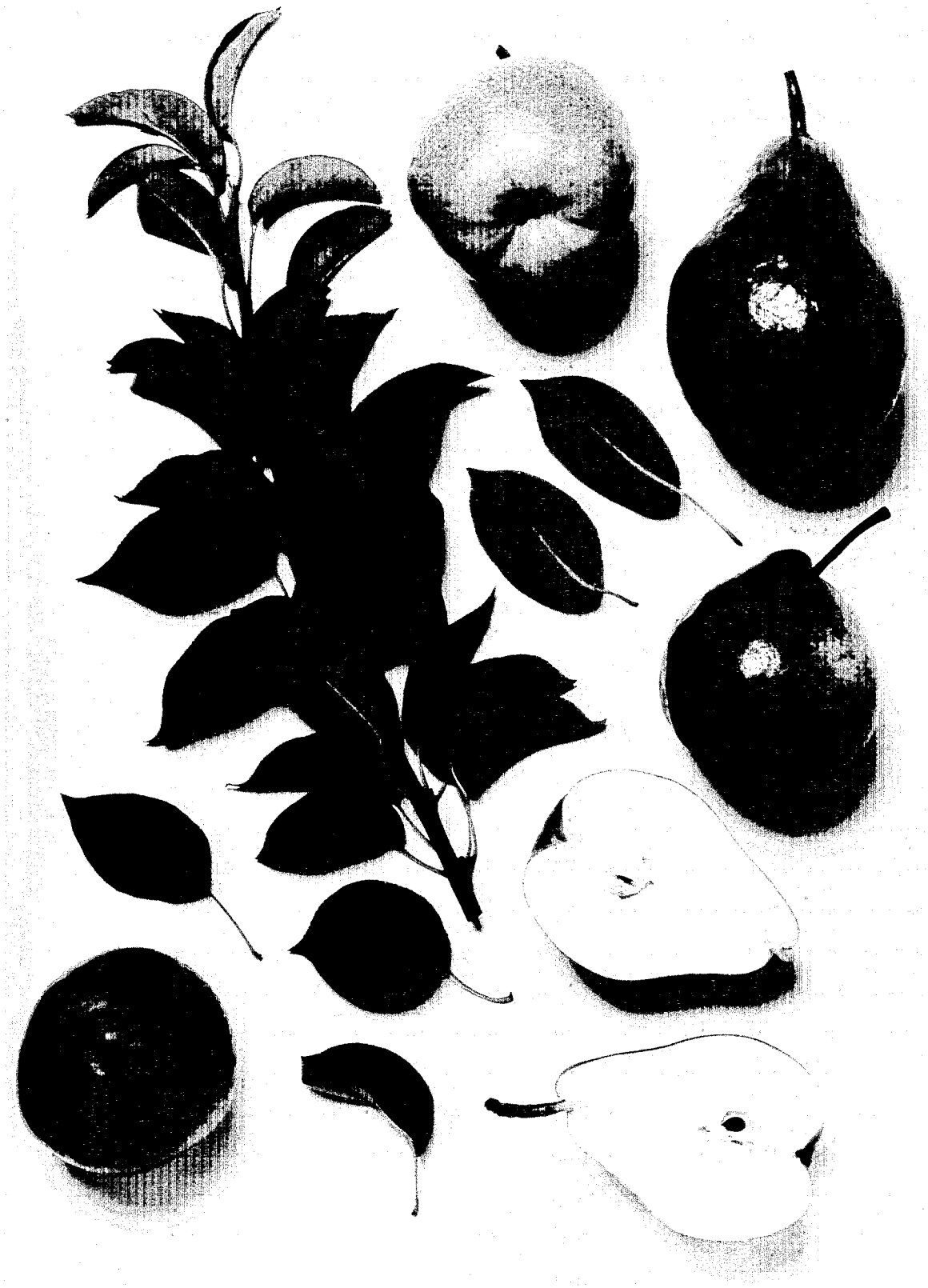

UNITED STATES PATENT AND TRADEMARK OFFICE

CERTIFICATE OF CORRECTION

PATENT NO. : Plant 7,730

DATED : December 3, 1991

INVENTOR(S) : David B. Lowry

It is certified that error appears in the above-identified patent and that said Letters Patent is hereby corrected as shown below:

Column 4, Line 12, CLEAVES should be LEAVES.

Signed and Sealed this

Second Day of March, 1993

*Attest:*

STEPHEN G. KUNIN

*Attesting Officer*

*Acting Commissioner of Patents and Trademarks*